US012649127B2

(12) United States Patent
Klopp et al.

(10) Patent No.: US 12,649,127 B2
(45) Date of Patent: Jun. 9, 2026

(54) FILTRATION SYSTEMS, COMPONENTS AND METHODS

(71) Applicant: ABEC, Inc., Bethlehem, PA (US)

(72) Inventors: Chris Klopp, Bethlehem, PA (US);
Colton Mitchell, Bethlehem, PA (US);
Evan Wait, Bethlehem, PA (US)

(73) Assignee: ABEC, Inc., Bethlehem, PA (US)

( * ) Notice: Subject to any disclaimer, the term of this patent is extended or adjusted under 35 U.S.C. 154(b) by 333 days.

(21) Appl. No.: 18/037,830

(22) PCT Filed: Nov. 22, 2021

(86) PCT No.: PCT/US2021/060264
§ 371 (c)(1),
(2) Date: May 19, 2023

(87) PCT Pub. No.: WO2022/109371
PCT Pub. Date: May 27, 2022

(65) Prior Publication Data
US 2024/0001304 A1     Jan. 4, 2024

Related U.S. Application Data

(60) Provisional application No. 63/117,365, filed on Nov. 23, 2020.

(51) Int. Cl.
*B01D 63/08*     (2006.01)
*C12M 1/00*     (2006.01)
(52) U.S. Cl.
CPC ........... *B01D 63/082* (2013.01); *C12M 47/12* (2013.01); *B01D 2313/18* (2013.01); *B01D*

2313/243 (2013.01); *B01D 2315/10* (2013.01); *B01D 2317/02* (2013.01)

(58) Field of Classification Search
None
See application file for complete search history.

(56) References Cited

U.S. PATENT DOCUMENTS

| | | | |
|---|---|---|---|
| 4,885,087 A | 12/1989 | Kopf | |
| 5,147,542 A | 9/1992 | Proulx | |
| 5,256,294 A | 10/1993 | Van Reis | |
| 5,342,517 A | 8/1994 | Kopf | |
| 7,306,727 B2 | 12/2007 | Perreault | |
| 7,674,885 B2 | 3/2010 | Konstantinov et al. | |
| 7,682,511 B2 | 3/2010 | De Los Reyes et al. | |
| 8,658,419 B2 | 2/2014 | Knight | |
| 9,174,171 B2 | 11/2015 | Weissenbach et al. | |
| 9,228,165 B2 | 1/2016 | Knight et al. | |

(Continued)

OTHER PUBLICATIONS

International Search Report for PCT/US2021/060264 (Oct. 2, 2022).

(Continued)

*Primary Examiner* — Krishnan S Menon
(74) *Attorney, Agent, or Firm* — Patrick J. Halloran

(57)     ABSTRACT

This disclosure generally relates to purification systems using tangential flow filtration ("TFF") ("TFF systems") that include at least one single-use, disposable flow path wherein the disposable flow path is comprised of a disposable cassette manifold, disposable tubing (including associated components) and a disposable reactor vessel.

15 Claims, 5 Drawing Sheets

(56) References Cited

U.S. PATENT DOCUMENTS

| | | | |
|---|---|---|---|
| 10,010,831 B2 | 7/2018 | Mangiacotti et al. | |
| 10,195,550 B2 | 2/2019 | Steen et al. | |
| 10,207,225 B2 | 2/2019 | Lutz et al. | |
| 10,370,456 B2 | 8/2019 | Winter | |
| 12,012,629 B2 | 6/2024 | Ransohoff et al. | |
| 12,351,793 B2 | 7/2025 | Mairesse et al. | |
| 2015/0004195 A1* | 1/2015 | Mundle ................... | C12N 7/00 |
| | | | 435/239 |
| 2017/0056825 A1* | 3/2017 | Schwan ................. | C12M 47/10 |
| 2018/0200673 A1 | 7/2018 | Benson et al. | |
| 2018/0221823 A1 | 8/2018 | Nutalapati et al. | |
| 2019/0298372 A1 | 10/2019 | Guerrera et al. | |
| 2020/0318060 A1 | 10/2020 | Castillo et al. | |
| 2024/0001329 A1 | 1/2024 | Rudolph et al. | |

OTHER PUBLICATIONS

Written Opinion for PCT/US2021/060264 (2022).
International Preliminary Report on Patentability for PCT/US2021/060264 (May 16, 2023).
EMD-Millipore-pellicon-xl50-cassette-data-sheet (2009).

* cited by examiner

FILTRATION SYSTEMS, COMPONENTS AND METHODS

RELATED APPLICATIONS

This application is a 35 U.S.C. § 371 national stage application of International Application No. PCT/US2021/060264, filed on Nov. 22, 2021, and claims priority to U.S. Ser. No. 63/177,365 filed on Nov. 23, 2020; each of which are hereby incorporated by reference in its entirety into this application.

FIELD OF THE DISCLOSURE

This disclosure relates to filtration systems, components, and methods related to the same.

BACKGROUND OF THE DISCLOSURE

This disclosure provides solutions to problems associated with the use of disposable components in tangential flow filtration (TFF) systems. For instance, a TFF system comprised of TFF filters (e.g. cassette filters) with a fully disposable flow path made of a disposable material is known not to provide sufficient volume capacity and/or resistance to pressures encountered during a large scale TFF process. This disclosure provides solutions to these and other art-recognized, and unrecognized, problems.

BRIEF DESCRIPTION OF THE DRAWINGS

FIG. 1. Exemplary view of disposable cassette manifold.

SUMMARY OF THE DISCLOSURE

Figure 1A:
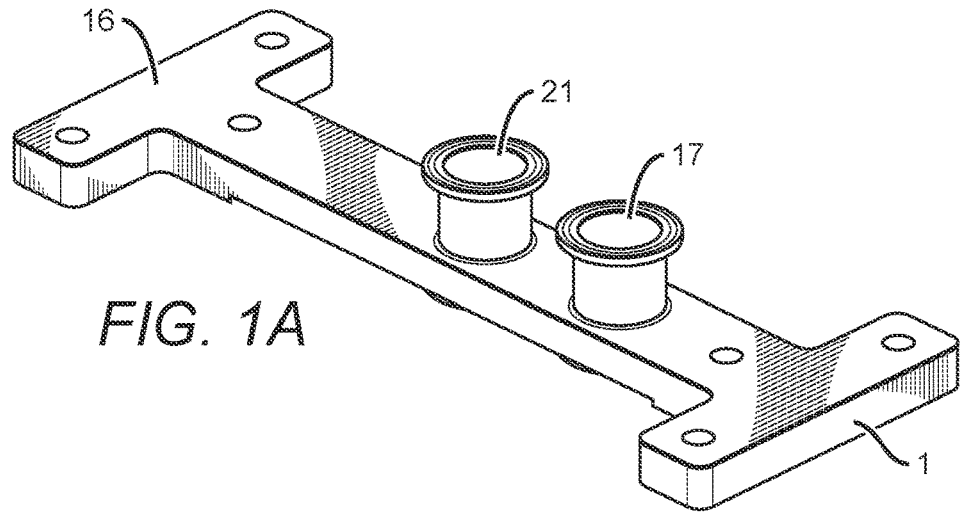
FIG. 1A illustrates an exemplary bottom piece.

This disclosure relates to tangential flow filtration (TFF) systems comprising a disposable cassette manifold and at least one TFF filter. In some embodiments, the disposable cassette manifold comprises a feed material inlet conduit, a permeate discharge conduit, and a retentate outlet conduit, wherein the multiple TFF filters provide approximately 5 m² to in excess of 40 m² surface area for filtration of feed material into retentate and permeate. In some embodiments, this disclosure relates to systems comprising one or more disposable cassette manifold and other components providing for the concentration, isolation and/or purification of a product from a feed material. In some embodiments, this disclosure also relates to methods for making and using such systems. Other embodiments are also contemplated as would be understood from this disclosure by those of ordinary skill in the art.

DETAILED DESCRIPTION

This disclosure generally relates to purification systems using tangential flow filtration ("TFF") ("TFF systems") that include at least one single-use, disposable cassette manifold fluidly connected to at least one TFF filter (e.g., filtration membrane and/or cassette filter). In various embodiments, such TFF systems can also include one or more conduits (e.g., tubing, piping) for feed, retentate and permeate, a housing or enclosure, valves, gaskets, a pump module (e.g., pump module comprising a pump housing, diaphragm and check valve) one or more vessels (e.g., reservoirs containers), and/or one or more pressure gauges. In some embodiments, the TFF systems can comprise at least one feed vessel, and at least one disposable retentate vessel, where at least one feed vessel and at least one disposable retentate vessel can be the same, one or more disposable permeate vessels, an optional disposable buffer vessel with one or more pumps and pump drives controlling the flow of feed material, retentate and/or permeate, at least one TFF filter coupled with a disposable cassette manifold (and in preferred embodiments multiple TFF filters), wherein such components are fluidly connected to one another such that feed and/or other materials can flow from and/or through one or more of the same, the system optionally comprising one or more valves that directs the flow of feed material, retentate and/or permeate to the various components of the system. In some embodiments, the feed vessel can be a jacketed vessel comprising at least one heat transfer element.

In some embodiments, this disclosure provides tangential flow filtration (TFF) systems comprising at least one disposable TFF cassette manifold and preferably multiple TFF filters within a single-use, disposable flow path. A single-use, disposable flow path refers to a flow path that directs flow of feed material, retentate, and permeate constructed of disposable materials (e.g., plastic, thermoplastic elastomer or similar). In preferred embodiments, the TFF system enables large scale operation by including high-pressure supply and return loops (e.g., feed material inlet conduit(s), permeate discharge conduit(s), retentate outlet conduit(s)) made of disposable semi-flexible hard plastic tubing (preferably having durometer of about 60 D, e.g., Kynar tubing) or braided reinforced silicon that are fluidly connected to the cassette manifold which distributes flow to and from the TFF filters and/or membrane(s) (e.g., TFF filter cassette(s)). In some embodiments, the TFF system includes one or more filtration units comprising a disposable cassette manifold with a feed material inlet conduit, a permeate discharge conduit, and a retentate outlet conduit, and multiple TFF filters of approximately 5 m² to in excess of 40 m² of total surface area being supplied with feed material. In some embodiments, this disclosure relates to systems comprising one or more TFF cassette holders and other components providing for the concentration, isolation and/or purification of a product (i.e. feed material).

In some embodiments, the disposable feed vessel can be a container in which a solution such as feed material and/or retentant can be maintained, separated from other components of a TFF system, and/or serve a source of material for processing through a TFF filter. In some embodiments, the feed vessel can take the form of a standard bioreactor or fermentation vessel as these are understood by those of ordinary skill in the art. In some embodiments, the feed vessel can be insulated, jacketed and/or include one or more heat transfer systems. In some embodiments, the vessel can have a form disclosed in, for instance and without limitation, U.S. Pat. No. 8,658,419 (ABEC, Inc.), U.S. Pat. No. 9,228,165 B2 (ABEC, Inc.), and/or WO 2019/070648 A2 (ABEC, Inc.). In some embodiments, the disposable feed vessel can be a cone-bottom or tulip-bottom vessel and/or preferably has a capacity of at least 20 L. Other types of suitable feed vessels that could be used as disclosed herein are also known in the art as would be understood by those of ordinary skill in the art.

In some embodiments, the TFF system can comprise a feed vessel fluidly connected to a feed pump that is fluidly connected to the disposable cassette manifold fluidly connected at least one TFF filter. In preferred embodiments, the disposable cassette manifold can be fluidly connected to a retentate outlet conduit and one or more valves controlling the flow of the retentate, and a permeate outlet conduit and one or more valves controlling the flow of the permeate. The retentate outlet conduit can be fluidly connected to a retentate vessel and/or a feed vessel. The retentate outlet conduit is typically fluidly connected to the feed vessel where the retentate is to be recirculated through the TFF filter(s). The permeate can be directed (i.e., fluidly connected) to a disposable permeate vessel. In some embodiments, the disposable feed vessel can also be fluidly connected to another disposable vessel such as diafiltration and/or buffer vessel(s). Any number of valves and/or controllers for directing the flow of feed material, permeate and/or retentate can be included in the TFF system, as would be understood by those of ordinary skill in the art.

In some embodiments, the disposable cassette manifold comprises one or more feed inlet(s) and/or one or more retentate outlet(s), and one or more permeate outlet(s). The disposable cassette manifold can also comprise multiple TFF filters through which the feed material traverses (which can be filter(s) or cassettes). In some embodiments, the feed material (e.g., fluid) enters the disposable cassette manifold and traverses through the TFF filter(s). As feed material passes through the TFF filter(s), it is typically separated into retentate and permeate. In some embodiments, the permeate can then be removed from the system (e.g., discarded) through the permeate outlet. In some embodiments, the retentate can be collected through the retentate outlet and directed to a storage vessel and/or back into the system (e.g., to the feed supply vessel) to be further processed (e.g., recirculated).

The TFF filters coupled (or "fluidly connected") to the disposable cassette manifold can be comprised of any suitable TFF filtration material that is available to those of ordinary skill in the art. Exemplary cassettes (e.g., TFF cassettes or cassette filters) suitable for use as described herein can comprise, but are not limited to Pellicon® cassettes such as those comprising Biomax™ membrane or Ultracel™ membrane (e.g., Pellicon® XL 50 cassettes, Pellicon® 2 cassettes, Pellicon® 2 Mini cassettes, Pellicon® 2 Maxi cassettes, Pellicon® 3 cassettes), TangenX® SUIS®, TangenX® PRO, Hydrosart® cassettes (Sartorius AG, Bohemia, N.Y.), Kvick™ Flow cassettes (GE Healthcare Bio-Sciences, Piscataway, N.J.), Prostak™ microfiltration modules, Prep/Scale® TFF cartridges), T-series cassettes with Delta membrane for Cadence™, TFF modules available from Pall Corporation (Port Washington, N.Y.); and/or as described in, for example and without limitation U.S. Pat. No. 5,256,294 (Genetech); U.S. Pat. No. 5,342,517 (Kopf, et al.); U.S. Pat. No. 7,306,727 B2 (Millipore Corp.); U.S. Pat. No. 7,674,885 B2 (Bayer Health Care); U.S. Pat. No. 10,370,456 B2 (Genentech/Novartis); U.S. Pat. Pub. No. 2018/0200673 A1 (Smartflow Techs.); and/or U.S. Pat. Pub. 2018/0298372 (CureVac); and the like. The TFF filters and/or cassettes can be arranged within the disposable cassette manifold in any suitable arrangement.

In some embodiments, the TFF system can include a plurality of filtration units comprising either multiple TFF filters and/or one or more TFF filters coupled with one or more disposable cassette manifolds, where each of the filtration units are directly or indirectly fluidly connected. The filtration units can be arranged for parallel processing and/or serial processing using conduits and/or valves that fluidly connect the units to one another. For instance, in some embodiments, filtration units can be operated in parallel when a valve between units is open, or in series when closed, and can alternate between various filtration units in a system such that some may operate in parallel with other units while others operate in series. In some embodiments, the filtration units can be stacked (e.g., vertically) to produce a stacked assembly with the use of one or more diverter or separator plates as is known in the art (e.g., (e.g., Pellicon® 2 Mini Holders separator plates (EMD Millipore, Billerica, Mass.). In some embodiments, all or less than all of the filtration units can be fluidly connected to one another. The filtration units can be fluidly connected in any suitable arrangement (e.g., in parallel and/or in series) as may be known or derived from the art, such as the systems described in U.S. Pat. No. 5,256,294 (Genetech); U.S. Pat. No. 5,342, 517 (Kopf, et al. (see, e.g., col. 17)); U.S. Pat. No. 7,306,727 B2 (Millipore Corp.); U.S. Pat. No. 7,674,885 B2 (Bayer Health Care); U.S. Pat. No. 10,370,456 B2 (Genentech/Novartis); U.S. Pat. Pub. No. 2018/0200673 A1 (Smartflow Techs.); and/or U.S. Pat. Pub. 2018/0298372 (CureVac); and similar references. In some embodiments, one or more valves can be fluidly connected to at least one of, or each of, the disposable cassette manifold(s).

The disposable cassette manifold, as well as any of the other components of the TFF system, can be made of disposable (e.g., single use), re-usable (e.g., sterilizable), and/or replaceable/swappable, the same being commercially available to those of ordinary skill in the art. In preferred embodiments, the components of the TFF system are made of disposable materials, preferably single use disposable materials. In even more preferred embodiments, at least the TFF cassette manifold(s) are made of disposable materials, preferably single use disposable materials. Exemplary, non-limiting components that can be included in the TFF systems can include Flexware® components (Mobius®), FlexReady Solution components (EMD Millipore Corporation), and/or Allegro™ components (Pall Corporation, Port Washington, N.Y.) In some embodiments, disposable feed and/or retentate conduits can be made from disposable tubing. In some embodiments, disposable components can be and/or can be used with other disposable components such as T line, valve (e.g., feed and/or retentate, or permeate vessel and/or conduit valve, such as a pinch or diaphragm valve). Typically such components are compatible with other components of the TFF system, are non-toxic, high-strength, sanitary, and/or re-usable. In some embodiments, the TFF system can also comprise one or more pressure sensor(s) (e.g., comprising a diaphragm) which may also be disposable and/or re-usable. In preferred embodiments, the components of the TFF system, individually and/or as one or more units thereof, can be sanitized (e.g., sterilized) prior to use, which can be carried out using standard techniques including but not limited to gamma radiation, ethylene oxide (ETO), bleach (e.g., Clorox), chlorine (e.g., NaOCl), peroxide, acid (e.g., peracetic acid), base (e.g., NaOH), formaldehyde (e.g., formaline solution) or heat, or an appropriate combination thereof.

Typically, a disposable TFF assembly of the invention includes a disposable flow path consisting of a disposable feed line, a disposable cassette manifold, a disposable retentate line, a disposable permeate line, and a disposable recirculation line or a combination thereof. The disposable components and disposable reactor vessel are made from disposable materials (e.g., plastic, thermoplastic elastomer, rubber, metal). Preferably, the disposable components and container are made from plastic, thermoplastic elastomer, or a combination of low-density and high-density polyethylene (LDPE and HDPE) or nylon.

Figure 1B:
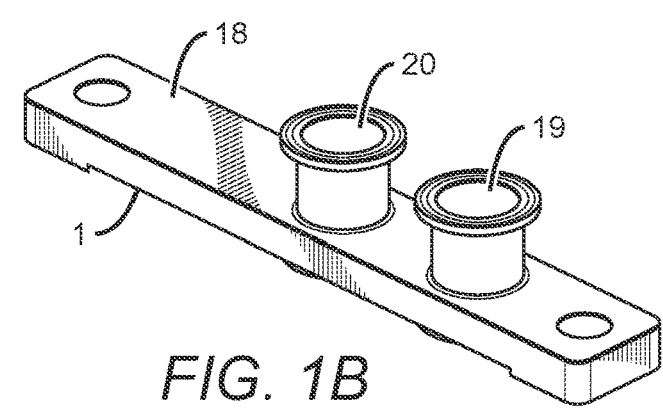
FIG. 1B illustrates an exemplary top piece.
Figure 1C:
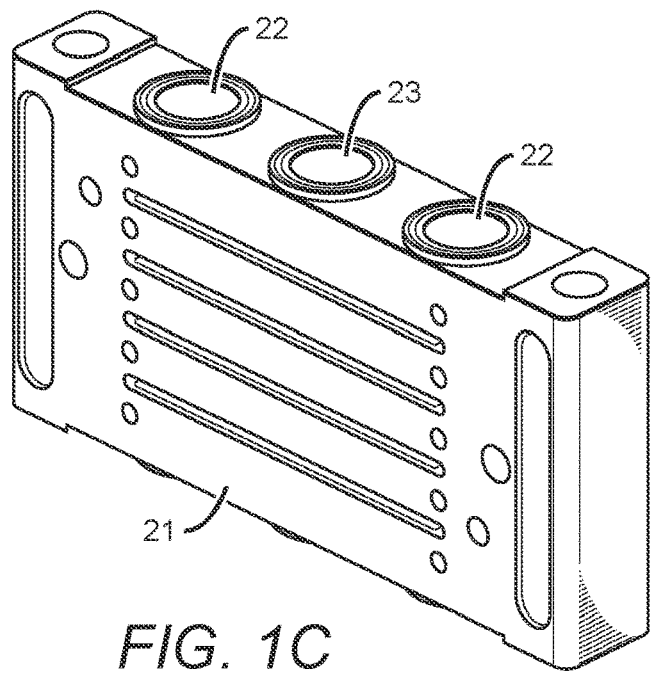
FIG. 1C illustrates one view of the single use disposable cassette manifold.

In preferred embodiments, the disposable cassette manifold can be arranged, and/or arranged within a TFF system, essentially as shown in any of FIGS. 1-5. As illustrated in the preferred embodiment of FIG. 1, the disposable cassette manifold can include a support base, at least one inlet for feed material, at least one outlet for retentate, and at least one outlet for permeate. A preferred embodiment of the TFF manifold is illustrated in FIG. 1. An exemplary bottom piece is illustrated in FIG. 1A and includes a bottom support base (16) and at least one manifold supply inlet (17) and one permeate drain (21). An exemplary top piece is illustrated in FIG. 1B with a top support base (18), at least one manifold outlet (19) and at least one permeate outlet (20). An exemplary disposable manifold is illustrated in FIG. 1C. In preferred embodiments, an assembled TFF cassette manifold includes the TFF manifold of FIG. 1C consisting of a TFF manifold (21) that further consists of a manifold inlet or outlet port (depending on orientation) (22) and a permeate port (either drain or outlet depending on orientation) (23), the bottom piece of FIG. 1A, and the top piece of FIG. 1B. In typical use, feed material and/or recirculated feed material enters the TFF filtration unit through the manifold supply inlet and filtered material (i.e. retentate) exits the TFF filtration unit through a manifold outlet where it can be directed to the recirculation pump, back to the Disposable Container (DC) within the DC holder and/or otherwise collected as filtered product (e.g., final product). Filtered product can also exit the TFF filtration unit through the permeate outlet and/or permeate drain that is not recirculated but is kept or disposed of as waste.

Figure 2:
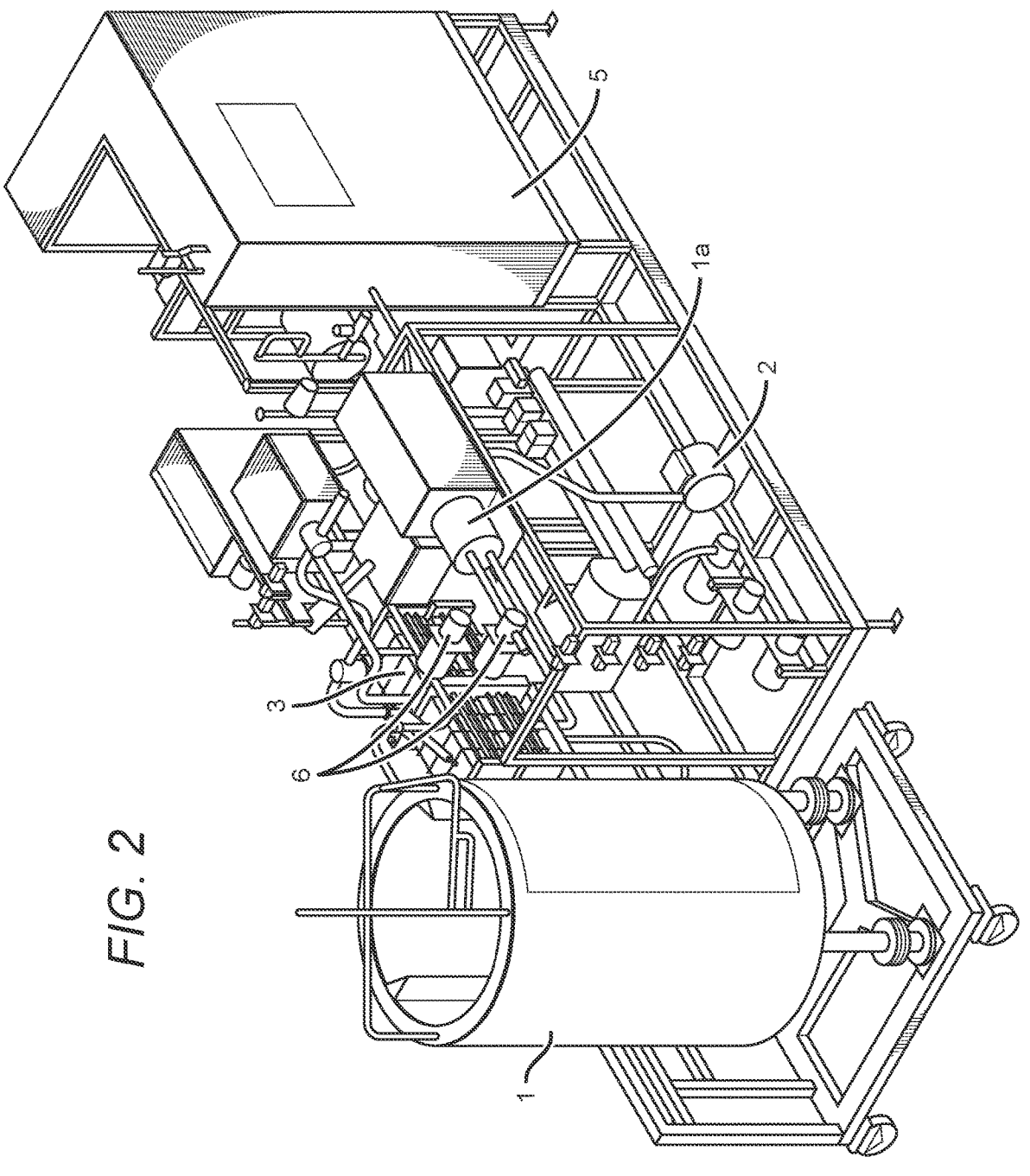
FIG. 2. Exemplary view of the TFF system.
Figure 3:
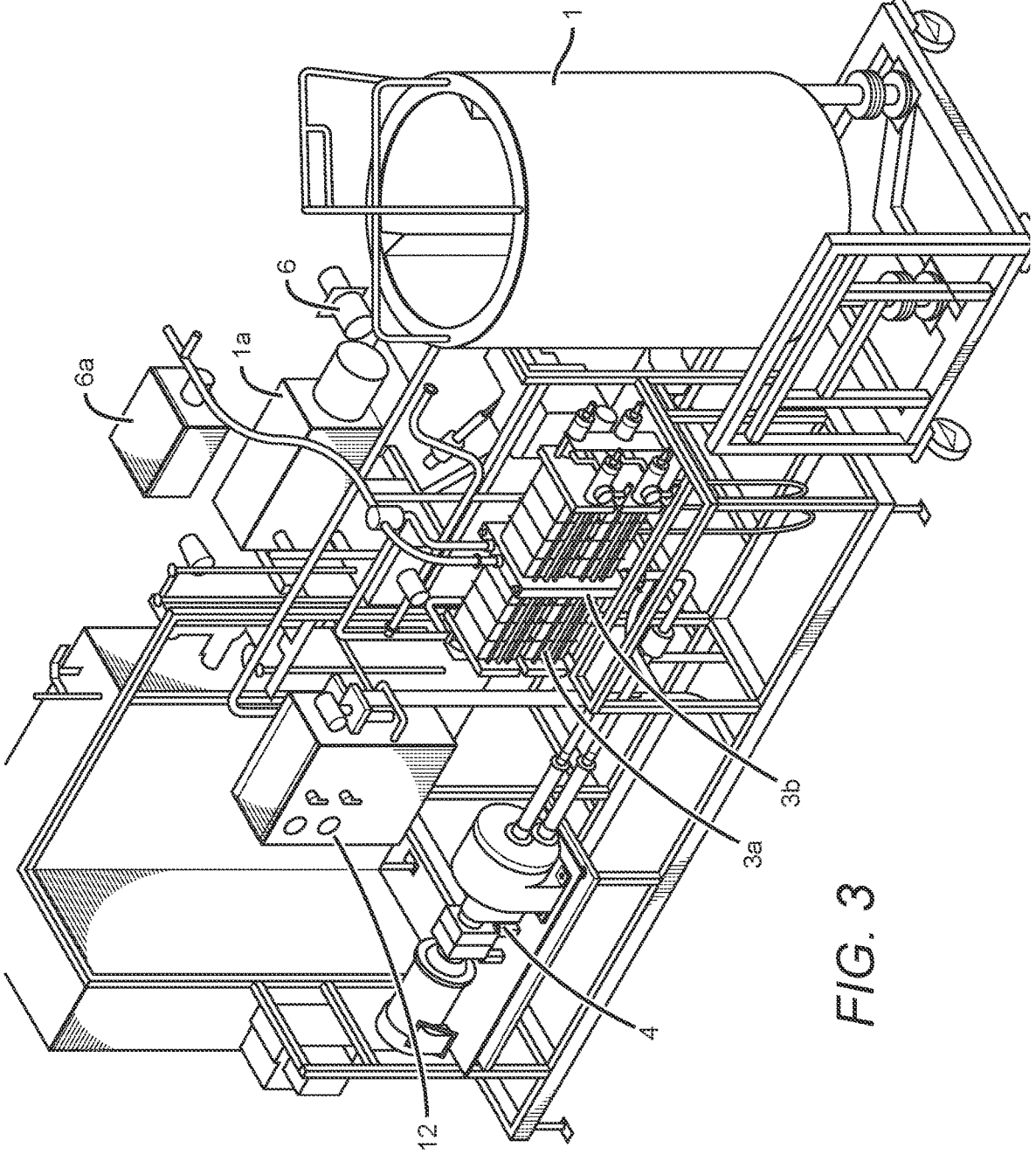
FIG. 3. Exemplary view of the TFF system.
Figure 4:
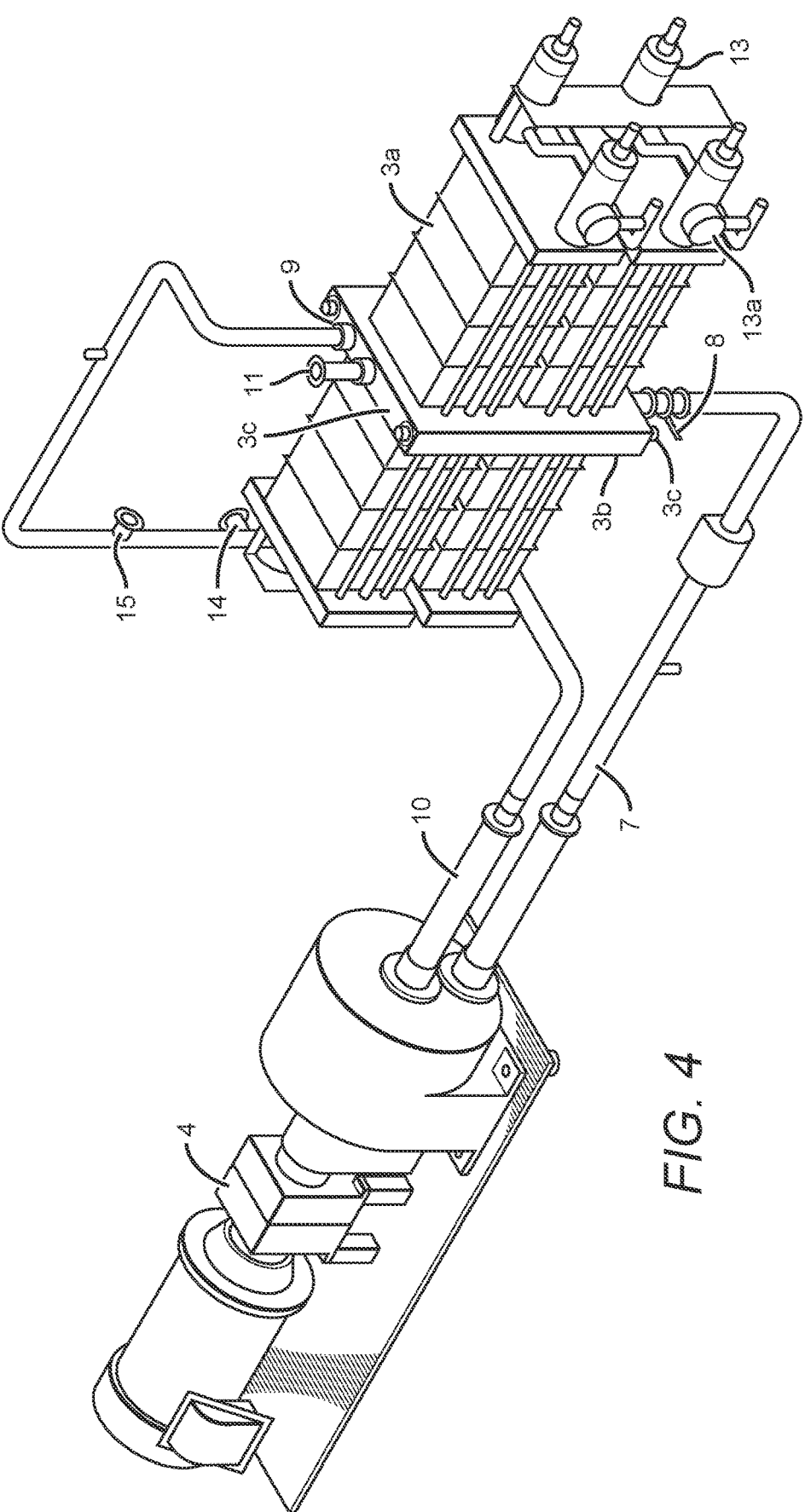
FIG. 4. Exemplary view of the high pressure disposable flow path of TFF system.
Figure 5:
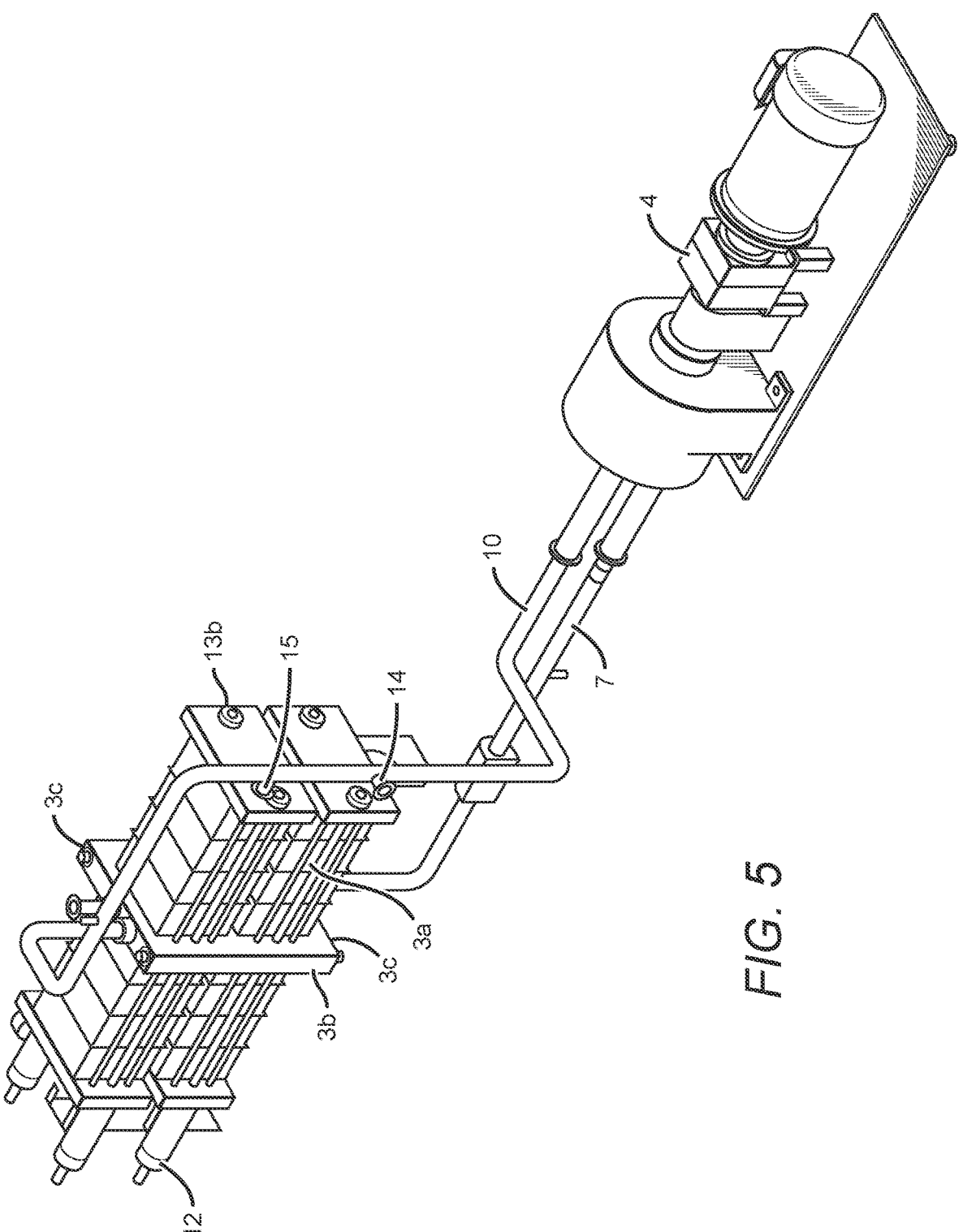
FIG. 5. Exemplary view of the high pressure disposable flow path of TFF system.

In preferred embodiments, such as those illustrated in FIGS. 2-3, the TFF system can include a single use reaction container (disposable container, "DC") within a DC holder (1), a buffer and/or product (to be processed by TFF) pump for supplying DC with product for filtering or buffer (1a), a feed pump (2) to supply the buffer and/or product into the recirculation loop, a single use disposable TFF filtration unit (3) including cassette filters (3a), a top and bottom piece (e.g., plate) (3c) and one or more, preferably two, disposable cassette manifold (3b) that directs retentate and permeate flow paths through the cassette filters (3a) (e.g., filtration media) and out into the recirculation loop (e.g., out the high-pressure return loop (10)), recirculation loop pump (4) for supplying/controllowing flow through the recirculation loop (7 (supply side) & 10 (return side)), electrical cabinet(s) including power and control systems (5) (e.g., control interface (HMI)), one or more valves (e.g., pinch valve(s)) to control flow (on, off, control)) of the various solutions distributed and used throughout the system (6, 6a), and hydraulic enclosure including controls for hydraulic pressure for the hydraulic cylinders (12) (e.g., preferably applies pressure to hold filter cassettes in place and pressed against cassette manifold). A preferred embodiment of the single use disposable TFF filtration unit is further illustrated in FIGS. 4-5, including recirculation loop pump (4), high-pressure supply loop (7) supplying the product to be filtered to the TFF cassettes (3a), the high-pressure supply loop (7) being supplied product through the feed supply inlet (14) from the feed pump (2) and being connected to one manifold inlet conduit (8) through which the TFF cassette filters (3a) are fed the product to be filtered, manifold outlet conduit (9)

from which TFF filtrate is fed into the high-pressure return loop (10) for recirculation or through the feed and/or retentate return outlet (15) for return to the DC holder (1), permeate discharge conduit (11) through which permeate (waste) is removed from the TFF filtration unit (e.g., to waste collection), along with one or more pressure gauges (13a) for monitoring pressure in the system, hydraulic cylinders (13) that apply pressure to the system to hold the TFF filter cassettes (3a) in position against the disposable cassette manifold (3b), and end plates that hold the filters in place (13b). In preferred embodiments, the DC, TFF filtration unit, disposable cassette manifold (3b), and high-pressure (e.g., Kynar) loop components (7, 10) consist of disposable or single use materials (e.g., thermoplastic elastomers, LDPE, HDPE). In preferred embodiments, the TFF cassette holder(s) can be arranged essentially as shown in any of FIGS. 1-5 and can be modified as appropriate and as would be understood by those of ordinary skill in the art. For instance, the positioning of components such as but not limited to electrical cabinet(s) and pinch valve(s) can vary from the positions illustrated by FIGS. 1-5. As illustrated in the preferred embodiment of FIG. 5, for instance, the TFF cassette holder(s) can include a support base, at least one inlet for feed material, at least one outlet for retentate, and at least one outlet for permeate. Other embodiments are also contemplated as would be understood by those of ordinary skill in the art.

In some embodiments, this disclosure provides tangential flow filtration (TFF) systems comprising a disposable TFF flow path comprising of a disposable cassette manifold, a first fluid pathway comprising low-pressure disposable tubing, a second fluid pathway comprising high-pressure disposable tubing, and a disposable reactor vessel. In some embodiments, the TFF system further comprises at least one a recirculation pump, wherein: the disposable reactor vessel is fluidly connected to the disposable low-pressure tubing and the recirculation pump; the recirculation pump is fluidly connected to a section of disposable high-pressure tubing (e.g., Kynar tubing) that supplies feed material the disposable cassette manifold (high-pressure supply loop); the recirculation pump is fluidly connected to a section of disposable high-pressure tubing that returns feed material from the disposable cassette manifold to the recirculation pump (high-pressure return loop); and, the disposable reactor vessel is not directly fluidly connected to the high-pressure disposable tubing. In preferred embodiments, the disposable cassette manifold comprises at least one feed material inlet conduit, at least one permeate discharge conduit, and at least one retentate outlet conduit, further preferably wherein each of the at least one feed material inlet conduit, at least one permeate discharge conduit, and at least one retentate outlet conduit are each fluidly connected to disposable high-pressure tubing. In preferred embodiments, the disposable cassette manifold can stably process feed material at a pressure of up to about 60 pounds per square inch (gauge) (psig) (e.g., Kynar tubing). In preferred embodiments, the disposable cassette manifold is comprised of plastic, optionally wherein the plastic comprises or consists of nylon or high-density polyethylene (HDPE). In preferred embodiments, the disposable high-pressure tubing has a Shore durometer of at least about 40 D, optionally at least about 50 D, and preferably about 60 D, as determined under the ASTM D2240 standard, a standard recognized by those of ordinary skill in the art. In other embodiments, the disposable high-pressure tubing can be braided tubing that can process the required pressure and flow rate. In preferred embodiments, the disposable cassette manifold is fluidly connected to one or more TFF filtration cassette(s) (as a filtration unit) that each (or in combination) provide approximately 5 m² to in excess of 40 m² surface area for filtration of feed material. In some embodiments, the TFF system can include multiple TFF cassettes fluidly connected in series, wherein feed material and optionally retentate flows from an initial TFF cassette to a terminal TFF cassette, optionally wherein at least one additional TFF cassette is positioned between the initial TFF cassette and the terminal TFF cassette. In some embodiments, the disposable reactor vessel is a cone-bottom or tulip-bottom vessel. In some embodiments, the disposable reactor vessel comprises the feed material and/or retentate. In some embodiments, the TFF system includes at least one valve for controlling flow into and/or from one or more of said filtration elements, said at least one valve being fluidly connected to at least one pump, optionally wherein at least one valve and/or at least one pump are controlled by a computer.

In preferred embodiments, this disclosure provides a disposable cassette manifold that: comprises at least one feed material inlet conduit, at least one permeate discharge conduit, and at least one retentate outlet conduit; can stably process feed material at a pressure of up to about 60 pounds per square inch (gauge) (psig); and, is comprised of plastic, optionally wherein the plastic comprises or consists of nylon or high-density polyethylene (HDPE). In some embodiments, the disposable cassette manifold can be fluidly connected to at least one tangential flow filtration (TFF) membrane.

In some embodiments, this disclosure provides methods for purifying and/or concentrating a product present within a feed material, the method comprising passing the feed material using a TFF system and/or a disposable cassette manifold of this disclosure. In some embodiments, the methods can include passing the feed material through the disposable cassette manifold and TFF cassette(s) to produce a retentate and isolating the retentate, and/or recirculating the retentate through the TFF cassettes to produce a purified and/or concentrated product. In preferred embodiments, the feed material is passed through the disposable cassette manifold and TFF cassette(s) pressure of up to about 60 pounds per square inch (gauge) (psig). In preferred embodiments, the methods include using a disposable cassette manifold comprised of plastic, optionally wherein the plastic comprises or consists of nylon or high-density polyethylene (HDPE).

In some embodiments, this disclosure provides methods for preparing a TFF system disclosed herein by, in some embodiments, fluidly connecting a disposable reactor vessel to the disposable low-pressure tubing and the recirculation pump; fluidly connecting the recirculation pump to a section of disposable high-pressure tubing that supplies feed material the disposable cassette manifold; fluidly connecting the recirculation pump to a section of disposable high-pressure tubing that returns feed material from the disposable cassette manifold to the recirculation pump, wherein the method does not comprise directly fluidly connecting the disposable reactor vessel to the high-pressure disposable tubing.

Other embodiments are also disclosed and/or contemplated and/or can be contemplated from this disclosure by those of ordinary skill in the art. Various embodiments of the present disclosure will be described in detail with reference to drawings, if any. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

The following terms are used herein, unless otherwise described. "Tangential flow filtration," (TFF) refers to filtration in which a product-containing solution (e.g., feed material) passes tangentially across a TFF filter membrane and lower molecular weight salts or solutes are passed through by applying pressure. "Feed material" refers to the solution being delivered to the TFF system for filtration and/or separation. "Separation" refers separating the feed material into at least two streams, typically permeate and retentate. "Permeate" refers to the portion of the feed material that has permeated through the membrane of the TFF filter. "Retentate" is the portion of the solution being filtered that has been retained by the TFF filter (i.e., membrane thereof), and the retentate is the fluid enriched for at least one protein that was present in the feed material. "Fluidly connecting" or "fluidly connected" is used indicates that the parts/components being connected to each other provide for the flow of fluid between such parts/components. "Flow path" refers to a channel (single pass or recirculation path) comprising a TFF membrane (e.g., ultrafiltration, microfiltration) through which a solution flows in TFF mode (e.g., and can be of any appropriate type including but not limited to straight, coiled, and/or serpentine, open, including obstructions, with or without spacers). A "filtration unit" is a disposable cassette manifold coupled with one or more TFF filters and/or TFF filtration cassettes. A "disposable cassette manifold" is a device supporting and coupled with one or more TFF filters and/or, preferably, TFF cassettes. A "TFF cassette" is a cartridge or structure comprising at least one TFF filtration membrane (e.g., ultrafiltration, microfiltration). "Filtration membrane" is a permeable membrane for separating feed material into permeate and retentate (by, e.g., ultrafiltration, microfiltration, reverse osmosis, and/or nanofiltration. "Ultrafiltering", "microfiltering", and like terms refer to, for example, using synthetic semi-permeable membranes, with appropriate physical and chemical properties, to discriminate between molecules in the mixture, primarily on the basis of molecular size and shape, and accomplish separation of different molecules or accomplish concentration of like molecules. In some embodiments, an "ultrafiltration membrane" is a membrane having pore sizes in the range of between about 1 nanometer to about 100 nanometers. In some embodiments, a "microfiltration membrane" is a membrane having a pore sizes in the range between about 0.1 micrometers to about 10 micrometers (including all values in between). "Diafiltering," "diafiltration," "diafiltered," "diafiltrating," "DF," and like terms refer to, for example, using an ultrafiltration membrane to remove, replace, or lower the concentration of salts or solvents from solutions or mixtures containing proteins, peptides, nucleic acids, or other biomolecules. "Fluidly connected" means that one TFF system component (e.g., disposable cassette manifold) is connected to another, and/or a different type of component, by at least one liquid conduit that provides for the flow of liquid between the TFF system components (e.g., a feed material conduit or channel, a retentate conduit or channel, a permeate conduit or channel). Fluidly connected parts or components, or parts or components sharing a "fluidic connection", are parts or components of the TFF system connected by a conduit or channel through which fluid (e.g., feed material, retentate, permeate) traverses the TFF system. A "direct" fluidic connection is one by which TFF system components are fluidly connected to on another such that the fluid does not flow through any intervening TFF system components (e.g., a TFF system component positioned between two other TFF system components). In some embodiments, for instance, the feed vessel is directly fluidly connected to low-pressure conduit but not high-pressure conduit or the recirculation pump, while the feed pump can be directly connected to both low-pressure conduit (e.g., from the feed vessel) and directly connected to high-pressure conduit (e.g., to and from the high pressure tubing). A "product" is a compound such as a protein (e.g., an antibody) that is present in a feed material that is being concentrated and/or isolated using the TFF system. "Parallel" refers to a TFF process in which a plurality of filtration units are fluidly connected such that the feed material is distributed from a feed inlet directly to each of the filtration units in the TFF system. "Serial" refers to a TFF process in which a plurality of filtration units are fluidly connected such that the feed material is distributed only to the initial filtration unit in the TFF system and/or in which subsequent filtration units receives their respective solution from preceding filtration unit. The term "vessel" refers to a tank, container, and/or reservoir that can hold or maintain fluid, and/or in some embodiments provide a source for feed and/or retentate.

This disclosure includes but is not limited to the following aspects:

1. A tangential flow filtration (TFF) system comprising a disposable TFF flow path comprising of a disposable cassette manifold, a first fluid pathway comprising low-pressure disposable tubing, a second fluid pathway comprising high-pressure disposable tubing, and a disposable reactor vessel.
2. A TFF system of aspect 1, the system further comprising at least one a recirculation pump, wherein:
   the disposable reactor vessel is fluidly connected to the disposable low-pressure tubing but not the recirculation pump;
   the recirculation pump is fluidly connected to a section of disposable high-pressure tubing that supplies feed material the disposable cassette manifold;
   the recirculation pump is fluidly connected to a section of disposable high-pressure tubing that returns feed material from the disposable cassette manifold to the recirculation pump; and,
   the disposable reactor vessel is not directly fluidly connected to the high-pressure disposable tubing.
3. The TFF system of any preceding aspect wherein the disposable cassette manifold comprises at least one feed material inlet conduit, at least one permeate discharge conduit, and at least one retentate outlet conduit.
4. The TFF system of any preceding aspect wherein the at least one feed material inlet conduit, at least one permeate discharge conduit, and at least one retentate outlet conduit are each fluidly connected to disposable high-pressure tubing.
5. The TFF system of any preceding aspect wherein the disposable cassette manifold can stably process feed material at a pressure of up to about 60 pounds per square inch (gauge) (psig).
6. The TFF system of any preceding aspect wherein the disposable cassette manifold is comprised of plastic, optionally wherein the plastic comprises or consists of nylon or high-density polyethylene (HDPE).
7. The TFF system of any preceding aspect wherein the disposable high-pressure tubing has a Shore durometer of at least about 40 D, optionally about 60 D or is braided reinforced silicon.
8. The TFF system of any preceding aspect wherein the disposable cassette manifold is fluidly connected to one or more TFF filtration cassette(s) that can provide approximately 5 m$^2$ to in excess of 40 m$^2$, surface area for filtration of feed material.
9. The TFF system of any preceding aspect comprising multiple TFF cassettes fluidly connected in series, wherein feed material and optionally retentate and permeate flows from an initial TFF cassette to a terminal TFF cassette, optionally wherein at least one additional TFF cassette is positioned between the initial TFF cassette and the terminal TFF cassette.
10. The TFF system of any preceding aspect wherein the disposable reactor vessel is a cone-bottom or tulip-bottom vessel.
11. The TFF system of any preceding aspect wherein the disposable reactor vessel comprises the feed material and/or retentate.
12. The TFF system of any preceding aspect further comprising at least one valve for controlling flow into and/or from one or more of said filtration elements, said at least one valve being fluidly connected to at least one pump.
13. The TFF system of aspect 12 wherein the at least one valve and at least one pump are controlled by a computer.
14. A disposable cassette manifold that: comprises at least one feed material inlet conduit, at least one permeate discharge conduit, and at least one retentate outlet conduit; can stably process feed material at a pressure of up to about 60 pounds per square inch (gauge) (psig); and, is comprised of plastic, optionally wherein the plastic comprises or consists of nylon or high-density polyethylene (HDPE).
15. The disposable cassette manifold of aspect 14 fluidly connected to at least one tangential flow filtration (TFF) membrane.
16. A method for purifying and/or concentrating a product present within a feed material, the method comprising passing the feed material using a system of any one of aspects 1-13 and/or a disposable cassette manifold of aspect 14 and/or 15.
17. The method of aspect 16 further comprising passing the feed material through the disposable cassette manifold and TFF cassette(s) to produce a retentate and isolating the retentate, and/or recirculating the retentate through the TFF cassettes to produce a purified and/or concentrated product.
18. The method of aspect 16 or 17 wherein the feed material is passed through the disposable cassette manifold and TFF cassette(s) pressure of up to about 60 pounds per square inch (gauge) (psig).
19. The method of any one of aspects 16-18 wherein the disposable cassette manifold is comprised of plastic, optionally wherein the plastic comprises or consists of nylon or high-density polyethylene (HDPE).
20. A method for preparing a TFF system of any one of aspects 1-13, the method comprising fluidly connecting a disposable reactor vessel to the disposable low-pressure tubing and the feed pump; fluidly connecting the recirculation pump to a section of disposable high-pressure tubing that supplies feed material the disposable cassette manifold; fluidly connecting the recirculation pump to a section of disposable high-pressure tubing that returns retentate material from the disposable cassette manifold to the recirculation pump, wherein the method does not comprise directly fluidly connecting the disposable reactor vessel to the high-pressure disposable tubing.

The terms "a", "an", and/or "the" typically means at least one, or one or more. The terms "about", "approximately", and the like, when used as a modifier refers to a variant of a number that typically occurs in carrying out standard procedures. In some preferred embodiments, "about", "approximately", and the like, indicates a numerical value of within ten percent (i.e., +/–10%) of the listed numerical value. The terms "about", "approximately", and the like, when preceding a list of numerical values or range, refer to each individual value in the list or range independently as if each individual value in the list or range was immediately preceded by that term. Optional or optionally means that the subsequently described event or circumstance can or cannot occur, and that the description includes instances where the event or circumstance occurs and instances where it does not. Ranges may be expressed herein as from about one particular value, and/or to about another particular value. When such a range is expressed, another aspect includes from the one particular value and/or to the other particular value. Similarly, when values are expressed as approximations, by use of the antecedent about or approximately, it will be understood that the particular value forms another aspect. It will be further understood that the endpoints of each of the ranges are significant both in relation to the other endpoint, and independently of the other endpoint. Ranges (e.g., 90-100%) are meant to include the range per se as well as each independent value within the range as if each value was individually listed.

All references cited within this disclosure are hereby incorporated by reference in their entirety. Certain embodiments are further described in the following examples. These embodiments are provided as examples only and are not intended to limit the scope of the claims in any way.

Other advantages of the reagents and methods of using the same are also provided herein, as would be understood by those of ordinary skill in the art. While certain embodiments have been described in terms of the preferred embodiments, it is understood that variations and modifications will occur to those skilled in the art. Therefore, it is intended that the appended claims cover all such equivalent variations that come within the scope of the following claims.

What is claimed is:

1. A tangential flow filtration (TFF) system providing a disposable flow path for processing a fluid feed material, the system comprising a disposable reactor vessel and a disposable TFF flow path comprising a disposable single use TFF filtration unit, wherein:

the disposable reactor vessel comprises feed material and/or buffer and is connected through disposable low-pressure tubing to a feed pump;

the disposable single use TFF filtration unit comprises:

a bottom support base comprising a manifold supply inlet and a permeate drain, and a top support base comprising a manifold outlet and a permeate outlet, and, cassette filters;

the feed pump is further connected through disposable high-pressure tubing to the manifold supply inlet;

a recirculation pump connected to a recirculation loop comprising a supply side conduit connected to the manifold supply inlet and a return side conduit connected to the manifold outlet, the supply side and return side conduits being comprised of disposable high-pressure tubing;

the return side conduit comprises a retentate return outlet for return of the feed and/or retentate to the disposable reactor vessel through low-pressure disposable tubing;

the disposable reactor vessel is not directly connected to the high-pressure disposable tubing;

the disposable reactor vessel, disposable low-pressure tubing, disposable high-pressure tubing, and disposable single use TFF filtration unit are comprised of plastic, thermoplastic elastomer, rubber, high-density polyethylene, a combination of low-density and high-density polyethylene, or nylon; and, the disposable high-pressure tubing has a Shore durometer of at least 40 D or is braided reinforced silicon.

2. The system of claim 1 wherein the disposable single use TFF filtration unit can stably process feed material at a pressure of up to about 60 pounds per square inch (psig).

3. The system of claim 1 wherein the disposable single use TFF filtration unit is comprised of plastic.

4. The system of claim 1 wherein the disposable high-pressure tubing has a Shore durometer of at least about 60 D.

5. The system of claim 1 wherein the disposable single use TFF filtration unit is fluidly connected to one or more TFF filtration cassette(s) providing approximately 5 m$^2$ to in excess of 40 m$^2$ surface area for filtration of feed material.

6. The system of claim 1 comprising multiple disposable single use TFF filtration units fluidly connected in series, wherein feed material flows from an initial TFF cassette to a terminal TFF cassette.

7. The system of claim 1 wherein the disposable reactor vessel is a cone-bottom or tulip-bottom vessel.

8. The system of claim 1 further comprising at least one valve for controlling flow into and/or from one or more of said filtration elements, said at least one valve being fluidly connected to at least one pump.

9. The system of claim 8 wherein the at least one valve and at least one pump are controlled by a computer.

10. The system of claim 1 wherein the disposable cassette manifold can stably process feed material at a pressure of up to about 60 pounds per square inch (psig).

11. A method for purifying and/or concentrating a product present within a feed material, the method comprising passing the feed material through using the system of claim 1.

12. The method of claim 11 further comprising passing the feed material through the disposable single use TFF filtration unit to produce a retentate and isolating the retentate, and/or recirculating the retentate through the disposable single use TFF filtration unit to produce a purified and/or concentrated product.

13. The method of claim 12 wherein the feed material is passed through the disposable single use TFF filtration unit at a pressure of up to about 60 pounds per square inch (psig).

14. The system of claim 6 wherein at least one additional TFF cassette is positioned between the initial TFF cassette and the terminal TFF cassette.

15. The system of claim 10 wherein the disposable cassette manifold is comprised of plastic comprising nylon and/or high-density polyethylene (HDPE).

* * * * *